(12) United States Patent
Hedrick et al.

(10) Patent No.: US 11,007,216 B2
(45) Date of Patent: May 18, 2021

(54) COMBINATION THERAPY TO ACHIEVE ENHANCED ANTIMICROBIAL ACTIVITY

(71) Applicants: International Business Machines Corporation, Armonk, NY (US); Agency for Science, Technology and Research, Singapore (SG)

(72) Inventors: James L. Hedrick, Pleasanton, CA (US); Yi Yan Yang, Singapore (SG); Xin Ding, Singapore (SG); Chuan Yang, Hillington Green (SG)

(73) Assignees: INTERNATIONAL BUSINESS MACHINES CORPORATION, Armonk, NY (US); AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 16/531,493

(22) Filed: Aug. 5, 2019

(65) Prior Publication Data
US 2021/0038635 A1  Feb. 11, 2021

(51) Int. Cl.
*A61K 31/765* (2006.01)
*A61K 33/242* (2019.01)

(52) U.S. Cl.
CPC .......... *A61K 31/765* (2013.01); *A61K 33/242* (2019.01)

(58) Field of Classification Search
CPC ............................ A61K 31/765; A61K 33/242
See application file for complete search history.

(56) References Cited

U.S. PATENT DOCUMENTS

| | | | |
|---|---|---|---|
| 9,854,806 B2 | 1/2018 | Chin et al. | |
| 9,976,074 B2 | 5/2018 | Stanciu et al. | |
| 2011/0311463 A1 | 12/2011 | Diamond et al. | |
| 2012/0045400 A1 | 2/2012 | Nowak et al. | |
| 2014/0193517 A1 | 7/2014 | Agarwal et al. | |
| 2015/0038671 A1 | 2/2015 | Parang et al. | |
| 2016/0338356 A1* | 11/2016 | Chin ...................... | C08G 18/73 |
| 2018/0020669 A1 | 1/2018 | Charles et al. | |
| 2018/0157786 A1 | 6/2018 | Dakshanamurthy et al. | |
| 2019/0388460 A1 | 12/2019 | Hedrick et al. | |

FOREIGN PATENT DOCUMENTS

| | | |
|---|---|---|
| CN | 108694991 A | 10/2018 |
| FR | 2851465 A1 | 8/2004 |
| WO | 2005/007098 A2 | 1/2005 |
| WO | 2016024999 A1 | 2/2016 |
| WO | 2016123368 A1 | 8/2016 |
| WO | 2016/186581 A1 | 11/2016 |
| WO | 2017053778 A1 | 3/2017 |
| WO | 2017066242 A1 | 4/2017 |
| WO | 2018015665 A1 | 1/2018 |

OTHER PUBLICATIONS

Cho et al. (Biomacromolecules, 2017, vol. 19, pp. 1389-1401, "Molecular Weight and Charge Density Effects of Guanidinylated Biodegradable Polycarbonates on Antimicrobial Activity and Selectivity") (Year: 2017).*
Ogrendik (International Journal of General Medicine, 2013, vol. 7, pp. 43-47) (Year: 2013).*
University of Minnesota (CIDRAP, Synthetic polymers show promise against-multidrug resistance, Apr. 9, 2018) (Year: 2018).*
Thangamani et al (Scientific Reports, 2016, vol. 6, pp. 1-13) (Year: 2016).*
Harbut et al. "Auranofin exerts broad-spectrum bactericidal activities by targeting thiol-redox homeostasis." Proceedings of the National Academy of Sciences. (2015). 6 pages.
Padhy et al. "Drug repositioning: Re-investigating existing drugs for new therapeutic indications." Journal Postgraduate Medicine 57(2), p. 153. (2011). 10 pages.
Younis et al. "Repurposing nonantimicrobial drugs and clinical molecules to treat bacterial infections." Current Pharmaceutical Design, 21(28), pp. 4106-4111. (2015). 11 pages.
Brochado et al. "Species-specific activity of antibacterial drug combinations" Nature International Journal of Science Jul. 4, 2018. 42 pages.
Chin et al., "A macromolecular approach to eradicate multidrug resistant bacterial infections while mitigating drug resistance onset", Nature Communications Article DOI: 10.1038/s41467-018-03325-6 (2018). 14 pages.
Piccaro et al., "Rifampin Induces Hydroxyl Radical Formation in *Mycobacterium tuberculosis*", AAC Journals.ASM.org Antimicrobial Agents and Chemotherapy p. 7527-7533 vol. 58 No. 12 Dec. 2014. 7 pages.
Hedrick, et al. "Utilizing Polymers and Antibiotics to Enhance Antimicrobial Activity and Inhibit Antibiotic Resistance." U.S. Appl. No. 16/144,040, filed Sep. 27, 2018. 56 pages.
Kolpin, Dana W., et al. "Pharmaceuticals, Hormones and Other Organic Wastewater Contaminants in U.S. Streams, 1999-2000: A National Reconnaissance." Environ. Sci. And Technol. 2002, 36, 1202-1211. 12 pages.
Hoque, Jiaul, et al. "Broad Spectrum Antibacterial and Antifungal Polymeric Paint Materials: Synthesis, Structure-Activity Relationship, and Membrane-Active Mode of Action." ACS Appl. Mater. Interfaces 2015, 7, 1804-1815. DOI: 10.1021/am507482y. 12 pages.
Non-Final Office Action received for U.S. Appl. No. 16/531,432 dated Aug. 24, 2020, 54 pages.
International Search Report and Written Opinion received for PCT Application Serial No. PCT/162020/056650 dated Nov. 3, 2020, 11 pages.

(Continued)

*Primary Examiner* — Mark V Stevens
(74) *Attorney, Agent, or Firm* — Amin, Turocy & Watson, LLP

(57) ABSTRACT

Techniques regarding enhancing antimicrobial activity of antirheumatic agents by combination therapy are provided. For example, one or more embodiments described herein can regard a chemical composition comprising a polycarbonate polymer functionalized with a guanidinium functional group. The chemical composition can also comprise an antirheumatic agent, and the polycarbonate polymer can enhance an antimicrobial activity of the antirheumatic agent.

20 Claims, 10 Drawing Sheets

(56) References Cited

OTHER PUBLICATIONS

El-Sersy et al., "Antibacterial and Anticancer activity of ε-poly-L-lysine (ε-Pl) produced by a marine Bacillus subtilis sp.", Journal of Basic Microbiology., vol. 52, Dec. 31, 2012, 10 pages.

Santos et al., "Recent Developments in Antimicrobial Polymers: A Review", Materials, vol. 9, Jul. 20, 2016, 33 pages.

Pantos et al., "Guanidinium group: A versatile moiety inducing transport and multicompartmentalization in complementary membranes", Biochimica et Biophysica Acta vol. 1778, Dec. 12, 2008, pp. 811-823.

Exley et al., "Antimicrobial Peptide Mimicking Primary Amine and Guanidine Containing Methacrylamide Copolymers Prepared by Raft Polymerization", Biomacromolecules., vol. 16 Nov. 11, 2015, pp. 3845-3852.

International Search Report and Written Opinion received for PCT Application Serial No. PCT/162020/056644 dated Nov. 3, 2020, 11 pages.

Song et al., β-methasone-containing biodegradable poly(lactide-coglycolide) acid microspheres for intraarticular injection: effect of formulation parameters on characteristics and in vitro release, Pharmaceutical Development and Technology, vol. 18, No. 5, Dec. 31, 2013, pp. 1220-1229.

Pearson et al., "Glycopolymer Self-Assemblies with Gold(I)Complexed to the Core as a Delivery System for Auranofin", Macromolecules, vol. 48, Jan. 23, 2015, pp. 118-125.

Dangol et al., "Innovative polymeric system (IPS) for solvent-free lipophilic drug transdermal delivery via dissolving microneedle", Journal of Controlled Release, vol. 223, Dec. 28, 2015, 25 pages.

* cited by examiner

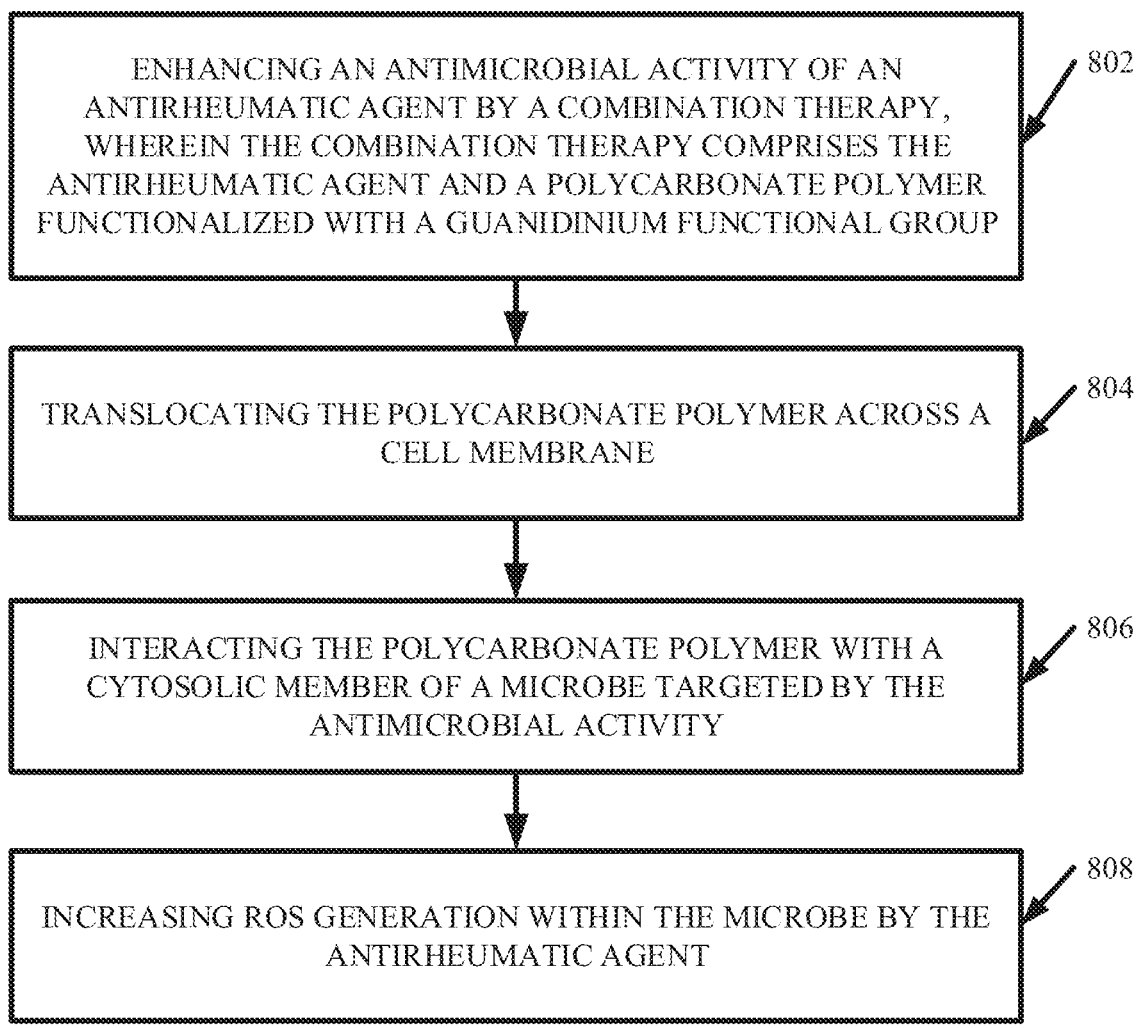

TREATING A BACTERIA INFECTION VIA A COMBINATION THERAPY THAT COMPRISES AN ANTIRHEUMATIC AGENT AND A POLYCARBONATE POLYMER FUNCTIONALIZED WITH A GUANIDINIUM FUNCTIONAL GROUP, WHEREIN THE POLYCARBONATE POLYMER ENHANCES AN ANTIBACTERIAL ACTIVITY OF THE ANTIRHEUMATIC AGENT ↙ 902

↓

INCREASING ROS GENERATION WITHIN A BACTERIUM OF THE BACTERIA INFECTION VIA THE ANTIRHEUMATIC AGENT ↙ 904

```
┌─────────────────────────────────────────────────────────┐
│ TREATING A BACTERIA INFECTION VIA A COMBINATION         │
│ THERAPY THAT COMPRISES AN ANTIRHEUMATIC AGENT AND A     │ ← 1002
│ POLYCARBONATE POLYMER FUNCTIONALIZED WITH A             │
│ GUANIDINIUM FUNCTIONAL GROUP, WHEREIN THE               │
│ POLYCARBONATE POLYMER ENHANCES AN ANTIBACTERIAL         │
│ ACTIVITY OF THE ANTIRHEUMATIC AGENT                     │
└─────────────────────────────────────────────────────────┘
                            │
                            ▼
┌─────────────────────────────────────────────────────────┐
│ TRANSLOCATING THE POLYCARBONATE POLYMER ACROSS A        │ ← 1004
│ CELL MEMBRANE OF A BACTERIUM OF THE BACTERIA            │
│ INFECTION                                               │
└─────────────────────────────────────────────────────────┘
                            │
                            ▼
┌─────────────────────────────────────────────────────────┐
│ PRECIPITATING A CYTOSOLIC MEMBER OF THE BACTERIUM VIA   │ ← 1006
│ AN INTERACTION BETWEEN THE CYTOSOLIC MEMBER AND THE     │
│ POLYCARBONATE POLYMER, WHEREIN THE CYTOSOLIC            │
│ MEMBER IS SELECTED FROM A GROUP CONSISTING OF A         │
│ PROTEIN, AN ENZYME, AND A GENE                          │
└─────────────────────────────────────────────────────────┘
                            │
                            ▼
┌─────────────────────────────────────────────────────────┐
│ INCREASING ROS GENERATION WITHIN A BACTERIUM OF THE     │ ← 1008
│ BACTERIA INFECTION VIA THE ANTIRHEUMATIC AGENT          │
└─────────────────────────────────────────────────────────┘
```

COMBINATION THERAPY TO ACHIEVE ENHANCED ANTIMICROBIAL ACTIVITY

BACKGROUND

The subject disclosure relates to the use of combination therapy to enhance antimicrobial activity of therapeutic compounds, and more specifically, to a combination therapy that comprises one or more poly(guanidinium carbonate) polymers and antirheumatic agents (e.g., Auranofin).

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, chemical compositions and/or method regarding one or more combination therapies comprising one or more poly(guanidinium carbonate) polymers and antirheumatic agents (e.g., Auranofin) are described.

According to an embodiment, a chemical composition is provided. The chemical composition can comprise a polycarbonate polymer functionalized with a guanidinium functional group. The chemical composition can also comprise an antirheumatic agent, and the polycarbonate polymer can enhance an antimicrobial activity of the antirheumatic agent.

According to an embodiment, a method is provided. The method can comprise enhancing an antimicrobial activity of an antirheumatic agent by a combination therapy. The combination therapy can comprise the antirheumatic agent and a polycarbonate polymer functionalized with a guanidinium functional group.

According to an embodiment, a method is provided. The method can comprise treating a bacteria infection via a combination therapy that comprises an antirheumatic agent and a polycarbonate polymer functionalized with a guanidinium functional group. Further, the polycarbonate polymer can enhance an antibacterial activity of the antirheumatic agent.

BRIEF DESCRIPTION OF THE DRAWINGS

FIG. 8 illustrates a flow diagram of an example, non-limiting method for enhancing the antimicrobial activity of one or more antirheumatic agents (e.g., Auranofin) in accordance with one or more embodiments described herein.

FIG. 9 illustrates a flow diagram of an example, non-limiting method for treating a bacteria infection via a combination therapy comprising one or more poly(guanidinium carbonate) polymers and antirheumatic agents (e.g., Auranofin) in accordance with one or more embodiments described herein.

FIG. 10 illustrates a flow diagram of an example, non-limiting method for treating a bacteria infection via a combination therapy comprising one or more poly(guanidinium carbonate) polymers and antirheumatic agents (e.g., Auranofin) in accordance with one or more embodiments described herein.

DETAILED DESCRIPTION

Figure 1:
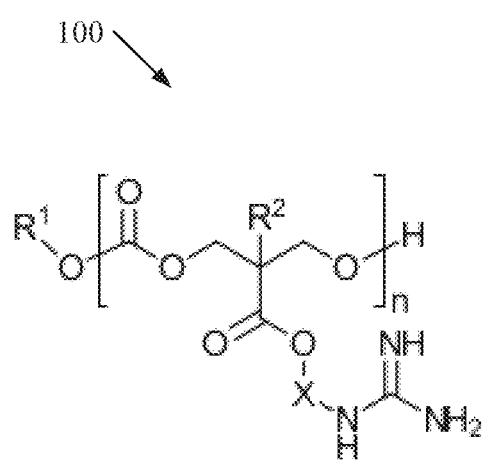
FIG. 1 illustrates a diagram of an example, non-limiting chemical formula that can characterize a poly(guanidinium carbonate) that can be comprised within a combination therapy with one or more antirheumatic agents (e.g., Auranofin) in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

There is a multitude of challenges associated with commercializing a new therapeutic chemical compound. For example, commercializing a new therapeutic chemical compound can cost, on average, 1.52 billion dollars, can take an average of 7 to 15 years, and/or can have a 90% failure rate. Additionally, regulatory limitations can be imposed onto newly introduced therapeutic chemical compounds. For example, newly introduced antibiotics can have regulatory limitations regarding availability as prescriptions and/or agricultural applications in order to minimize the development of antibiotic resistivity amongst bacteria.

Various embodiments described herein can regard repositioning one or more antirheumatic agents as antimicrobial agents (e.g., with antibacterial activity) using a combination therapy with one or more poly(guanidinium carbonate) polymers in accordance with one or more embodiments described herein. One or more embodiments can regard a chemical composition comprising one or more polycarbonate polymers functionalized with a guanidinium functional group, and one or more antirheumatic agents (e.g., Auranofin). The one or more polycarbonate polymers can enhance an antimicrobial activity of the one or more antirheumatic agents. For example, the one or more polycarbonate polymers can interact with a subject microbe via a translocation mechanism and precipitate one or more cytosolic members. Precipitation of the one or more cytosolic members can enable antimicrobial activity by the one or more antirheumatic agents that would have otherwise been inhibited. For instance, the one or more polycarbonate polymers can enable the one or more antirheumatic agents to increase generation of reactive oxygen species ("ROS") within the microbe. Thereby, the one or more polycarbonate polymers can enhance the antimicrobial activity of the one or more antirheumatic agents and/or enable the repositioning of the one or more antirheumatic agents as broad spectrum antimicrobials to treat bacterial infections.

As used herein, the term "combination therapy" can refer to the use of multiple chemical compounds to treat an illness and/or disease. The chemical compounds can comprise pharmaceutical compounds, such as antirheumatic agents and/or antibiotics. Additionally, the chemical compounds can comprise compounds other than pharmaceutical compounds, such as antimicrobial polymers (e.g., functionalized polycarbonates). The multiple chemical compounds can be used in combination to achieve one or more synergistic effects, which can enhance and/or facilitate one or more therapeutic treatments of the chemical compounds. In addition, the combination can comprise various types of chemical compounds. For example, one or more pharmaceutical compounds can be combined with one or more antimicrobial polymers in one or more combination therapies. Further, treating the illness can comprise: inhibiting the illness, eradicating the illness, delaying the illness, mitigating the illness, reducing the development of a resistance to treatment by the illness, a combination thereof, and/or the like. Moreover, the illness (e.g., an infection) can be caused by one or more microbes (e.g., bacteria, such as Gram-negative bacteria).

Unless otherwise stated, materials utilized to facilitate the experiments, tables, charts, diagrams, and/or the like described herein can be acquired from the following sources. The bacteria *Acinetobacter baumannii* ("*A. baumannii*"), *Enterobacter aerogenes* ("*E. aerogenes*"), *Escherichia coli* ("*E. coli*"), *Pseudomonas aeruginosa* ("*P. aeruginosa*"), and/or *Klebsiella pneumoniae* (*K. pneumoniae*) can be acquired from American Type Culture Collection ("ATCC"). Also, the antirheumatic agent Auranofin can be acquired from Sigma-Aldrich.

FIG. 1 illustrates a diagram of an example, non-limiting chemical structure 100 that can characterize one or more poly(guanidinium carbonate) polymers that can be utilized in combination with one or more antirheumatic agents in one or more combination therapies directed against one or more bacteria (e.g., one or more antibiotic-resistant bacteria and/ or Gram-negative bacteria) in accordance with one or more embodiments. Repetitive description of like elements employed in other embodiments described herein is omitted for sake of brevity.

The chemical structure 100 shown in FIG. 1 can characterize one or more guanidium-functionalized polycarbonate polymers that can be utilized in combination with one or more antirheumatic agents in accordance with one or more embodiments described herein. As shown in FIG. 1, the chemical structure 100 can comprise one or more functional groups. For instance, "$R^1$", as shown in FIG. 1, can represent a first functional group. The first functional group can comprise, for example, one or more: biotin groups, sugar groups, alkyl groups, and/or aryl groups. For example, the one or more first functional groups (e.g., represented by "$R^1$") can comprise, but are not limited to: carboxyl groups, carbonyl groups, ester groups, ether groups, ketone groups, amine groups, phosphine groups, urea croups, carbonate groups, alkenyl groups, hydroxyl groups, a combination thereof, and/or the like. Additionally, "$R^2$", as shown in FIG. 1, can represent a second functional group. The second functional group can comprise, for example, one or more alkyl groups and/or aryl groups. For example, the one or more second functional groups (e.g., represented by "$R^2$") can comprise, but are not limited to: carboxyl groups, carbonyl groups, ester groups, ether groups, ketone groups, amine groups, phosphine groups, urea croups, carbonate groups, alkenyl groups, hydroxyl groups, a combination thereof, and/or the like. Moreover, "X", as shown in FIG. 1, can represent one or more spacer structures. The one or more spacer structures can comprise, for example, one or more alkyl groups and/or aryl groups. For example, the one or more spacer structures (e.g., represented by "X") can comprise, but are not limited to: carboxyl groups, carbonyl groups, ester groups, ether groups, ketone groups, amine groups, phosphine groups, urea croups, carbonate groups, alkenyl groups, hydroxyl groups, a combination thereof, and/or the like. Lastly, "n", as shown in FIG. 1, can represent a number greater than or equal to one. For example, "n" can represent a number ranging from, for example, greater than or equal to one and less than or equal to 1000 (e.g., 20). As shown in FIG. 1, the one or more polycarbonates characterized by the chemical structure 100 can be functionalized with one or more guanidinium groups (e.g., bonded to the one or more polycarbonates via the one or more spacer structures "X"). In one or more embodiments, the one or more guanidinium groups can be cationic (e.g., due to protonation of a primary amine of the guanidinium group).

Figure 2:
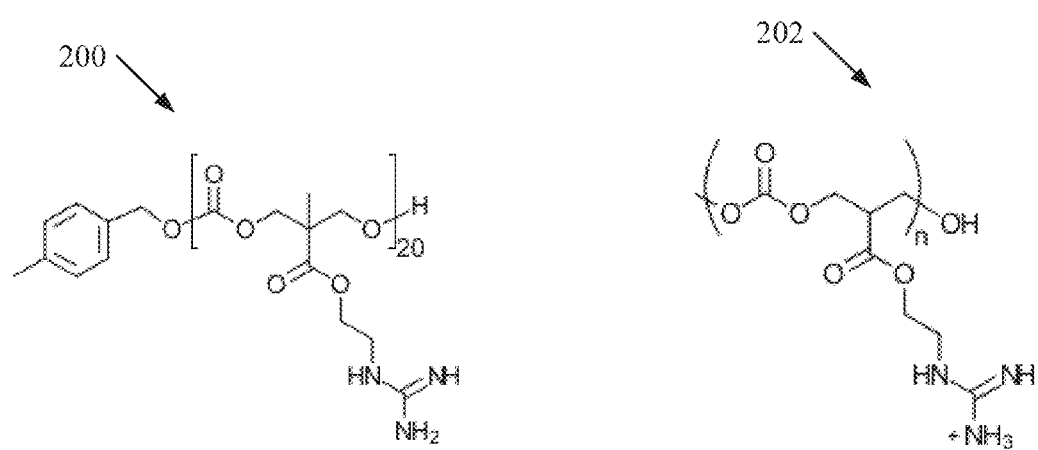
FIG. 2 illustrates a diagram of example, non-limiting poly(guanidinium carbonate) structures that can be comprised within a combination therapy with one or more antirheumatic agents (e.g., Auranofin) in accordance with one or more embodiments described herein.

FIG. 2 illustrates a diagram of example, non-limiting polymers that can be utilized in conjunction with one or more antirheumatic agents to facilitate one or more combination therapies in accordance with one or more embodiments described herein. Repetitive description of like elements employed in other embodiments described herein is omitted for sake of brevity. For example, FIG. 2 depicts a first example polycarbonate 200 and/or a second example polycarbonate 202. The first example polycarbonate 200 and/or the second example polycarbonate 202 can be characterized by chemical structure 100. Also, as shown in FIG. 2, "n" shown can represent a number greater than or equal to two and less than or equal to one thousand.

Figure 3:
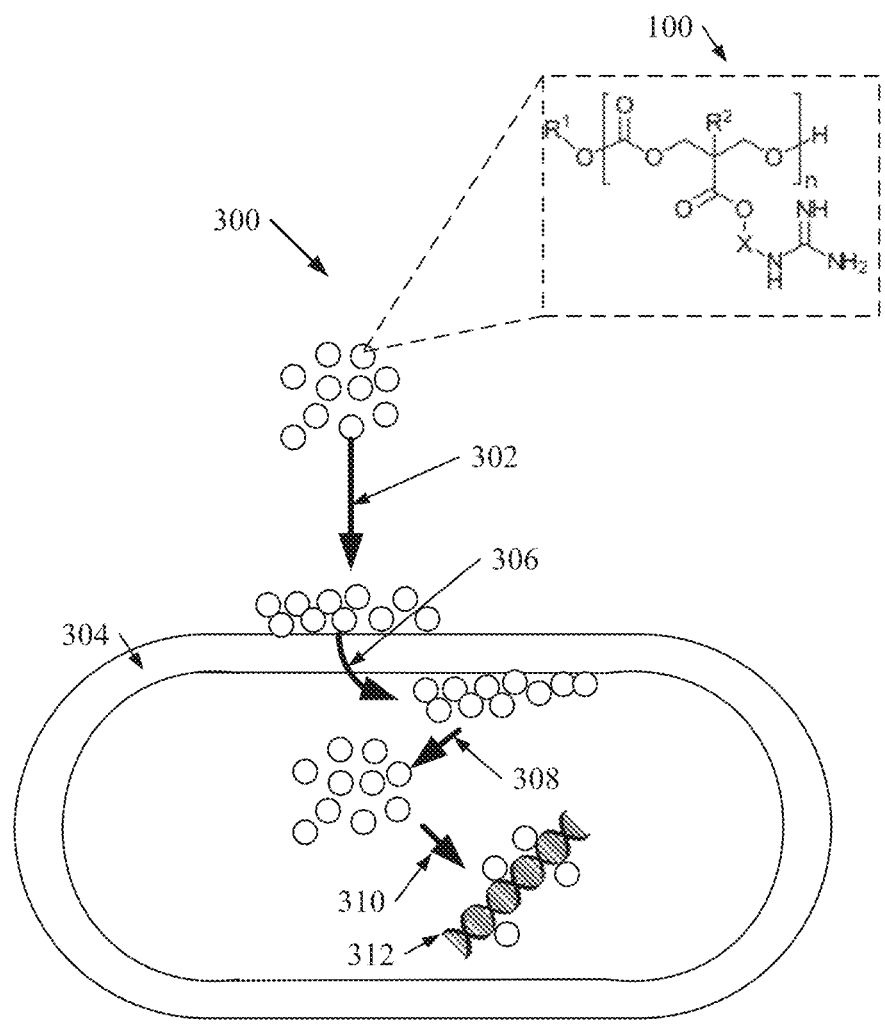
FIG. 3 illustrates a diagram of an example, non-limiting translocation mechanism that can be implemented by one or more poly(guanidinium carbonate) polymers comprised within a combination therapy with one or more antirheumatic agents (e.g., Auranofin) in accordance with one or more embodiments described herein.

FIG. 3 illustrates a diagram of an example, non-limiting translocation mechanism 300 that can be implemented by one or more combination therapies, which can utilize one or more polymers characterized by the chemical structure 100 in conjunction with one or more antirheumatic agents in accordance with one or more embodiments described herein.

Repetitive description of like elements employed in other embodiments described herein is omitted for sake of brevity. In one or more embodiments, the translocation mechanism 300 can be directed towards one or more bacteria. Exemplary bacteria can include Gram-negative bacteria and/or Gram-positive bacteria.

In one or more embodiments, one or more poly(guanidinium carbonate) polymers (e.g., characterized by chemical structure 100) can undergo translocation mechanism 300 with one or more bacteria. At a first stage 302 of the translocation mechanism 300, one or more poly(guanidinium carbonate) polymers (e.g., represented by circles and/or characterized by chemical structure 100) can be attracted to the cell membrane 304 of a target microbe (e.g., a bacterium). In one or more embodiments, the one or more poly(guanidinium carbonate) polymers can be electrostatically attracted towards the cell membrane 304. For example, one or more guanidinium groups of the poly(guanidinium carbonate) polymers can be cationic and/or can be electrostatically attracted to one or more negative charges associated with the cell membrane 304.

At a second stage 306, the one or more poly(guanidinium carbonate) polymers can pass through the cell membrane 304 of the subject microbe and enter an interior of the microbe. For instance, the cell membrane 304 (e.g., comprising a lipid bilayer) can separate the interior of the subject microbe from the environment surrounding the subject microbe. In various embodiments, the one or more guanidinium functional groups of the one or more poly(guanidinium carbonate) polymers can form one or more multidentate hydrogen-bonds with one or more phosphate groups in the cell membrane 304. The one or more multidentate hydrogen-bonds can neutralize a charge of the cell membrane 304, and thus can promote cell membrane 304 translocation. Upon entering the microbe, the one or more poly(guanidinium carbonate) polymers can associate with an inner leaflet of the cell membrane 304 (e.g., as shown in FIG. 3).

At a third stage 308, the one or more poly(guanidinium carbonate) polymers can be released from the inner leaflet and be dispersed within a cytoplasm of the microbe. At a fourth stage 310, the one or more poly(guanidinium carbonate) polymers can precipitate one or more proteins, enzymes, and/or genes (e.g., located in one or more DNA segments 312 of the microbe). For instance, the one or more poly(guanidinium carbonate) polymers can interact with one or more cytosolic proteins, enzymes, and/or genes of the microbe and/or precipitate the cytosolic members.

In one or more embodiments, the one or more antirheumatic agents can treat rheumatoid arthritis by inhibiting thioredoxin reductase in targeted cells. Thioredoxin reductase can maintain intercellular levels of ROS. Thus, inhibition of thioredoxin reductase can result in enhanced levels of ROS and cell apoptosis. For instance, the antirheumatic agent (2,3,4,6-Tetra-O-acetyl-1-thio-β-D-glucopyranosato-κS$^1$)(triethylphosphoranylidene)gold ("Auranofin") can function by increasing ROS generation in targeted cells. However, some microbes (e.g., Gram-negative bacteria) can comprise one or more cytosolic members that can inhibit the function of the antirheumatic agents (e.g., thereby avoiding enhanced ROS generation and cell apoptosis).

In various embodiments, the one or more cytosolic members (e.g., proteins, enzymes, and/or genes) that can inhibit the function of the one or more antirheumatic agents can be targeted for binding and/or precipitation by the one or more poly(guanidinium carbonate) polymers during the translocation mechanism 300. Thereby, the one or more poly (guanidinium carbonate) polymers, which can be characterized by the chemical structure 100, can enhance the antimicrobial activity of the one or more antirheumatic agents (e.g., Auranofin) by binding and/or precipitating one or more cytosolic proteins, enzymes, and/or genes of the target microbe. For example, the antibacterial activity of Auranofin towards Gram-negative bacteria can be enhanced via a combination therapy comprising one or more poly (guanidinium carbonate) polymers that can be characterized by chemical structure 100, wherein cytosolic members that could otherwise inhibit the function of Auranofin can be precipitated by the one or more poly(guanidinium carbonate) polymers through a translocation mechanism 300.

Figure 4:
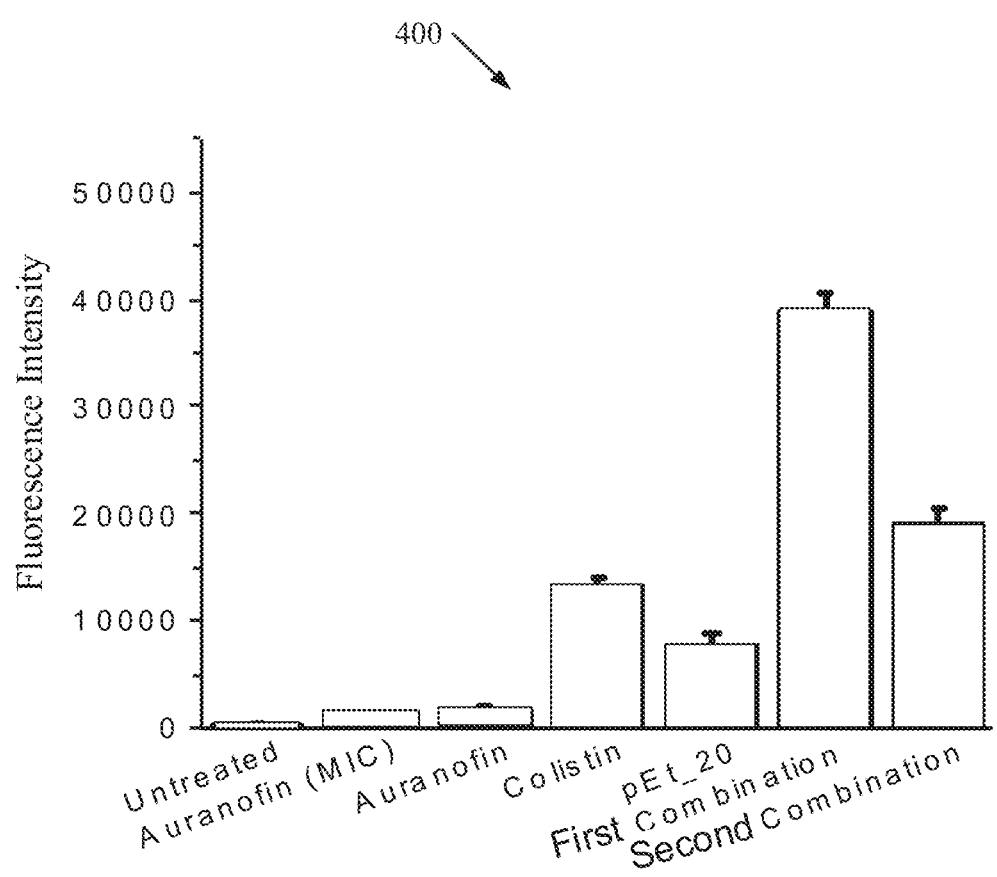
FIG. 4 illustrates a diagram of an example, non-limiting bar graph that can depict the efficacy of a combination therapy that comprises one or more poly(guanidinium carbonate) polymers and antirheumatic agents (e.g., Auranofin) in accordance with one or more embodiments described herein.

FIG. 4 illustrates a diagram of an example, non-limiting bar graph 400 that can exemplify the enhanced antimicrobial activity of Auranofin resulting from a combination therapy with one or more poly(guanidinium carbonate) polymers that can be characterized by chemical structure 100 in accordance with one or more embodiments described herein. Repetitive description of like elements employed in other embodiments described herein is omitted for sake of brevity. Bar graph 400 monitors the ROS generation within *A. baumannii* cells treated with minimum inhibitory concentrations ("MIC") of Auranofin, Colistin, first example polycarbonate 200, and/or a combination thereof.

To derive bar graph 400, $10^7$ colony-forming units ("CFU") per milliliter (mL) of *A. baumannii* were treated for 10 minutes with Auranofin, Colistin, first example polycarbonate 200, and/or a combination thereof. A CellRox green fluorescent probe was used to measure cellular oxidative stress. For example, the cell-permeable dye can exhibit fluorescence upon oxidation by ROS. Thereby, the greater the amount of ROS generation within the cells, the greater the fluorescence intensity and the greater the cell apoptosis.

The "untreated" bar can represent ROS generation in *A. baumannii* cells that were not treated with Auranofin, Colistin, first example polycarbonate 200, and/or a combination thereof. The "Auranofin (MIC)" bar can represent ROS generation in *A. baumannii* cells that were treated with an MIC of 15.6 micrograms per mL (µg/mL) of Auranofin. The "Auranofin" bar can represent ROS generation in *A. baumannii* cells that were treated with one half the MIC of Auranofin (e.g., 7.8 µg/mL of Auranofin). The "Colistin" bar can represent ROS generation in *A. baumannii* cells that were treated with one half the MIC (1 µg/mL) of Colistin (e.g., 0.5 µg/mL of Colistin). The "pEt_20" bar can represent ROS generation in *A. baumannii* cells that were treated with one half the MIC (15.6 µg/mL) of first example polycarbonate 200 (e.g., 7.8 µg/mL of first example polycarbonate 200). The "first combination" bar can represent ROS generation in *A. baumannii* cells that were treated with a combination therapy comprising 7.8 µg/mL of Auranofin and 7.8 µg/mL of first example polycarbonate 200. The "second combination" bar can represent ROS generation in *A. baumannii* cells that were treated with a combination therapy comprising 7.8 µg/mL of Auranofin and 0.5 µg/mL of Colistin.

As shown in FIG. 4, antimicrobial activity of the antirheumatic agent Auranofin can be greatly enhanced through combination therapy with one or more poly(guanidinium carbonate) polymers characterized by chemical structure 100 (e.g., first example polycarbonate 200). Additionally, FIG. 4 illustrates that a combination therapy comprising Auranofin and the one or more poly(guanidinium carbonate) polymers can have an even greater antimicrobial affect than the use of the poly(guanidinium carbonate) polymers alone. Moreover, FIG. 4 illustrates that a combination therapy comprising Auranofin and the one or more poly(guanidinium carbonate) polymers can have an even greater antimicrobial affect than the use of the strong antibacterial agent Colistin (e.g., either alone or in a combination therapy).

Figure 5A:
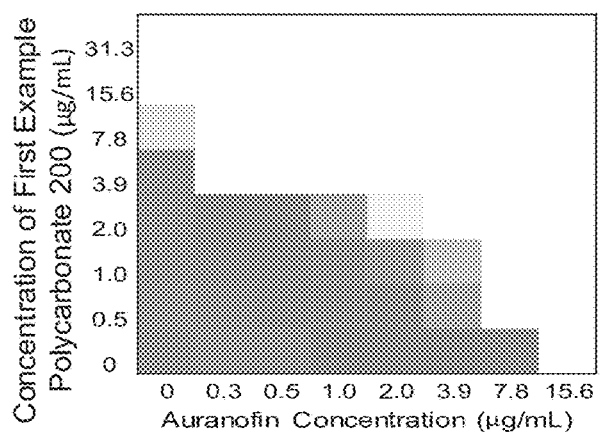
FIG. 5A illustrates a diagram of an example, non-limiting graph that can depict the efficacy of a combination therapy that comprises one or more poly(guanidinium carbonate) polymers and antirheumatic agents (e.g., Auranofin) in accordance with one or more embodiments described herein.
Figure 5B:
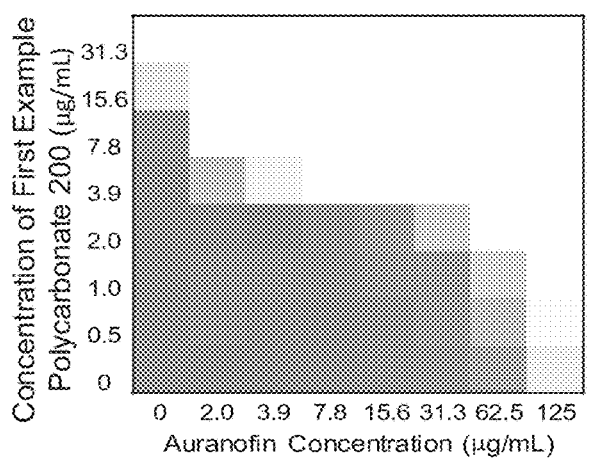
FIG. 5B illustrates a diagram of an example, non-limiting graph that can depict the efficacy of a combination therapy that comprises one or more poly(guanidinium carbonate) polymers and antirheumatic agents (e.g., Auranofin) in accordance with one or more embodiments described herein.

FIGS. 5A-B and/or 6A-B illustrate diagrams of example, non-limiting graphs that can further demonstrate the efficacy of a combination therapy comprising one or more antirheumatic agents and poly(guanidinium carbonate) polymers in the treatment of various bacteria infections in accordance with one or more embodiments described herein. Repetitive description of like elements employed in other embodiments described herein is omitted for sake of brevity.

Figure 6A:
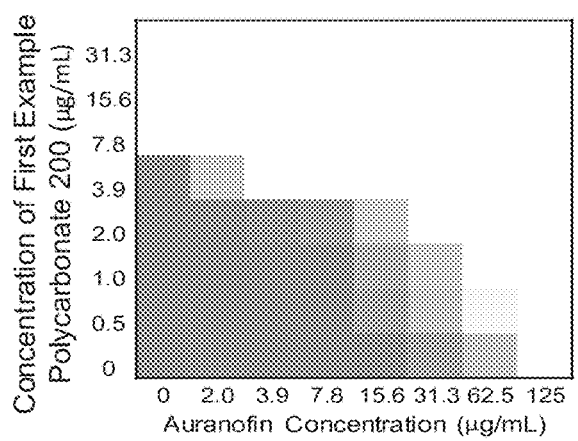
FIG. 6A illustrates a diagram of an example, non-limiting graph that can depict the efficacy of a combination therapy that comprises one or more poly(guanidinium carbonate) polymers and antirheumatic agents (e.g., Auranofin) in accordance with one or more embodiments described herein.
Figure 6B:
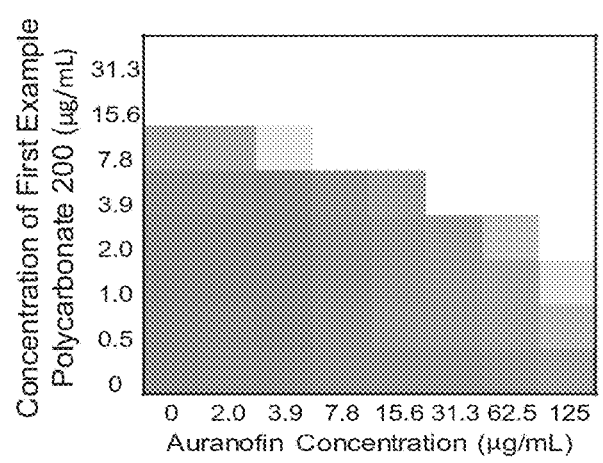
FIG. 6B illustrates a diagram of an example, non-limiting graph that can depict the efficacy of a combination therapy that comprises one or more poly(guanidinium carbonate) polymers and antirheumatic agents (e.g., Auranofin) in accordance with one or more embodiments described herein.

FIG. 5A regards treatment of *A. baumannii* with an exemplary combination therapy comprising Auranofin and the first example polycarbonate 200, wherein the MIC of the combination therapy equals 0.13 µg/mL. FIG. 5B regards treatment of *E. aerogenes* with an exemplary combination therapy comprising Auranofin and the first example polycarbonate 200, wherein the MIC of the combination therapy equals 0.13 µg/mL. FIG. 6A regards treatment of *E. coli* with an exemplary combination therapy comprising Auranofin and the first example polycarbonate 200, wherein the MIC of the combination therapy equals 3.90 µg/mL. FIG. 6B regards treatment of *K. pneumoniae* with an exemplary combination therapy comprising Auranofin and the first example polycarbonate 200, wherein the MIC of the combination therapy equals 7.80 µg/mL.

FIGS. 5A-B and/or 6A-B demonstrate that the combination therapies described herein can exhibit greater antimicrobial activity towards bacteria (e.g., Gram-negative bacteria) than is otherwise exhibited by the antirheumatic agents (e.g., Auranofin) or poly(guanidinium carbonate) polymers alone. For example, Auranofin typically exhibits little to no antimicrobial activity towards Gram-negative bacteria; however, the one or more combination therapies described herein can enhance the antimicrobial activity of Auranofin such that the antimicrobial functionality of Auranofin (e.g., increased ROS generation within targeted cells) can be effective in treating (e.g., inhibiting) Gram-negative bacteria. For instance, the translocation mechanism 300 exhibited by the one or more poly(guanidinium carbonate) polymers described herein can have a synergistic effect with the thioredoxin reductase inhibition exhibited by Auranofin; thereby, enhancing the antimicrobial activity of Auranofin via combination therapy with one or more of the various poly(guanidinium carbonate) polymers described herein.

Figure 7:
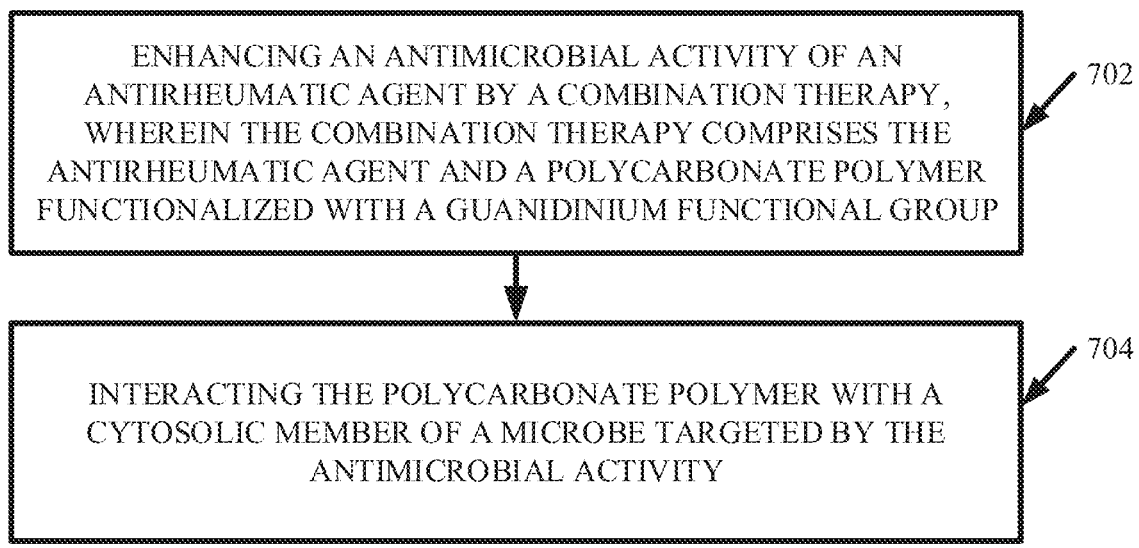
FIG. 7 illustrates a flow diagram of an example, non-limiting method for enhancing the antimicrobial activity of one or more antirheumatic agents (e.g., Auranofin) in accordance with one or more embodiments described herein.

FIG. 7 illustrates a flow diagram of an example, non-limiting method 700 regarding one or more combination therapies comprising one or more poly(guanidinium carbonate) polymers and antirheumatic agents in accordance with one or more embodiments described herein. Repetitive description of like elements employed in other embodiments described herein is omitted for sake of brevity.

At 702, the method 700 can comprise enhancing an antimicrobial activity of one or more antirheumatic agents by a combination therapy, wherein the combination therapy can comprise the one or more antirheumatic agents and one or more polycarbonate polymers functionalized with one or more guanidinium functional groups. For example, the one or more antirheumatic agents can be Auranofin and/or the one or more polycarbonate polymers can be characterized by chemical structure 100 (e.g., first example polycarbonate 200 and/or second example polycarbonate 202). In various embodiments, the antimicrobial activity can be antibacterial activity effective in treating one or more bacteria infections, such as infections of Gram-negative bacteria.

At 704, the method 700 can comprise interacting the one or more polycarbonate polymers with one or more cytosolic members of a microbe targeted by the antimicrobial activity. For example, the one or more polycarbonate polymers can implement a translocation mechanism (e.g., translocation mechanism 300) to bind and/or precipitate the one or more cytosolic members. Example cytosolic members can include, but are not limited to: proteins, enzymes, and/or genes. In various embodiments, the interacting at 704 by the one or more polycarbonate polymers can have a synergistic effect with the antimicrobial activity of the one or more antirheumatic agents. For example, the one or more cytosolic members targeted by the interacting at 704 can be cytosolic members that would otherwise inhibit one or more antimicrobial functionality of the one or more antirheumatic agents; thereby facilitating the enhancing of antimicrobial activity at 702. In one or more embodiments, the one or more antirheumatic agents can be Auranofin and the combination therapy can enable the Auranofin to exhibit antimicrobial activity towards Gram-negative bacteria.

FIG. 8 illustrates a flow diagram of an example, non-limiting method 800 regarding one or more combination therapies comprising one or more poly(guanidinium carbonate) polymers and antirheumatic agents in accordance with one or more embodiments described herein. Repetitive description of like elements employed in other embodiments described herein is omitted for sake of brevity.

At 802, the method 800 can comprise enhancing an antimicrobial activity of one or more antirheumatic agents by a combination therapy, wherein the combination therapy can comprise the one or more antirheumatic agents and one or more polycarbonate polymers functionalized with one or more guanidinium functional groups. For example, the one or more antirheumatic agents can be Auranofin and/or the one or more polycarbonate polymers can be characterized by chemical structure 100 (e.g., first example polycarbonate 200 and/or second example polycarbonate 202). In various embodiments, the antimicrobial activity can be antibacterial activity effective in treating one or more bacteria infections, such as infections of Gram-negative bacteria.

At 804, the method 800 can comprise translocating the one or more polycarbonate polymers across a cell membrane 304. For example, the translocating at 804 can be performed in accordance with the translocation mechanism 300 described herein. For instance, the cell membrane 304 can be the membrane of a microbe targeted by the antimicrobial activity of the one or more antirheumatic agents.

At 806, the method 800 can comprise interacting the one or more polycarbonate polymers with one or more cytosolic members of a microbe targeted by the antimicrobial activity. For example, following the translocation at 804, the one or more polycarbonate polymers can bind and/or precipitate the one or more cytosolic members. Example cytosolic members can include, but are not limited to: proteins, enzymes, and/or genes. In various embodiments, the one or more cytosolic members targeted by the interacting at 806 can be cytosolic members that would otherwise inhibit one or more antimicrobial functionality of the one or more antirheumatic agents.

At 808, the method 800 can comprise increasing ROS generation within the microbe by the one or more antirheumatic agents. For example, the one or more antirheumatic agents can inhibit thioredoxin reductase within the microbe. In various embodiments, increasing the ROS generation at 808 can be enabled, at least in part, by the translocating at 804 and/or interacting at 806 performed by the one or more polycarbonate polymers. Thus, the activity of the one or more polycarbonate polymers can have a synergistic effect with the activity of the one or more antirheumatic agents and thereby facilitate enhancing the antimicrobial activity.

FIG. 9 illustrates a flow diagram of an example, non-limiting method 900 regarding one or more combination therapies comprising one or more poly(guanidinium carbonate) polymers and antirheumatic agents in accordance with one or more embodiments described herein. Repetitive description of like elements employed in other embodiments described herein is omitted for sake of brevity.

At 902, the method 900 can comprise treating a bacteria infection via a combination therapy that comprises one or more antirheumatic agents and one or more polycarbonate polymers functionalized with one or more guanidinium functional groups, wherein the one or more polycarbonate polymers can enhance an antibacterial activity of the one or more antirheumatic agents. For example, the one or more antirheumatic agents can be Auranofin and/or the one or more polycarbonate polymers can be characterized by chemical structure 100 (e.g., first example polycarbonate 200 and/or second example polycarbonate 202). Further, example bacteria infections can include, but are not limited to, infections of: *A. baumannii, E. aerogenes, E. coli, K. pneumoniae*, a combination thereof, and/or the like.

At 904, the method 900 can comprise increasing ROS generation within one or more bacteria of the bacteria infection via the one or more antirheumatic agents. For example, the one or more polycarbonate polymers of the combination therapy can enable and/or facilitate thioredoxin reductase inhibition activity by the one or more antirheumatic agents. Thereby, the one or more antirheumatic agents can exhibit enhanced antibacterial activity. For example, Auranofin can exhibit antibacterial activity towards Gram-negative bacteria.

FIG. 10 illustrates a flow diagram of an example, non-limiting method 1000 regarding one or more combination therapies comprising one or more poly(guanidinium carbonate) polymers and antirheumatic agents in accordance with one or more embodiments described herein. Repetitive description of like elements employed in other embodiments described herein is omitted for sake of brevity.

At 1002, the method 1000 can comprise treating a bacteria infection via a combination therapy that comprises one or more antirheumatic agents and one or more polycarbonate polymers functionalized with one or more guanidinium functional groups, wherein the one or more polycarbonate polymers can enhance an antibacterial activity of the one or more antirheumatic agents. For example, the one or more antirheumatic agents can be Auranofin and/or the one or more polycarbonate polymers can be characterized by chemical structure 100 (e.g., first example polycarbonate 200 and/or second example polycarbonate 202). Further, example bacteria infections can include, but are not limited to, infections of: *A. baumannii, E. aerogenes, E. coli, K. pneumoniae*, a combination thereof, and/or the like.

At 1004, the method 1000 can comprise translocating the one or more polycarbonate polymers across a cell membrane 304 of one or more bacteria of the bacteria infection. For example, the translocating at 1004 can be performed in accordance with the translocation mechanism 300 described herein. For instance, the cell membrane 304 can be the membrane of a bacterium targeted by the antibacterial activity of the one or more antirheumatic agents.

At 1006, the method 800 can comprise precipitating one or more cytosolic members of the one or more bacteria via an interaction between the one or more cytosolic members and the one or more polycarbonate polymers. For example, following the translocation at 1004, the one or more polycarbonate polymers can bind and/or precipitate the one or more cytosolic members. Example cytosolic members can include, but are not limited to: proteins, enzymes, and/or genes. In various embodiments, the one or more cytosolic members targeted by the interacting at 1006 can be cytosolic members that would otherwise inhibit one or more antimicrobial functionality of the one or more antirheumatic agents.

At 1008, the method 1000 can comprise increasing ROS generation within the one or more bacteria by the one or more antirheumatic agents. For example, the one or more antirheumatic agents can inhibit thioredoxin reductase within the microbe. In various embodiments, increasing the ROS generation at 1008 can be enabled, at least in part, by the translocating at 1004 and/or interacting at 1006 performed by the one or more polycarbonate polymers. Thus, the activity of the one or more polycarbonate polymers can have a synergistic effect with the activity of the one or more antirheumatic agents and thereby facilitate enhancing the antibacterial activity.

Throughout the present disclosure, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

It is, of course, not possible to describe every conceivable combination of components, products and/or methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A chemical composition comprising:
   a polycarbonate polymer functionalized with at least one guanidinium functional group; and an antirheumatic agent comprising (2,3,4,6-Tetra-O-acetyl-1-thio-β-D-glucopyranosato-κS¹)(triethylphosphoranylidene)gold, wherein the chemical composition provides antimicrobial activity against Gram-negative bacteria.

2. The chemical composition of claim 1, wherein the polycarbonate polymer facilitates translocating the antirheumatic agent across a cell membrane and interacting the antirheumatic agent with a cytosolic member of a Gram-negative bacterium.

3. The chemical composition of claim 2, wherein the cytosolic member is selected from the group consisting of a protein, an enzyme, and a gene.

4. The chemical composition of claim 1, wherein the antimicrobial activity comprises enhancing reactive oxygen species generation within the Gram-negative bacteria.

5. The chemical composition of claim 1, wherein the polycarbonate polymer has a structure characterized by a chemical formula:

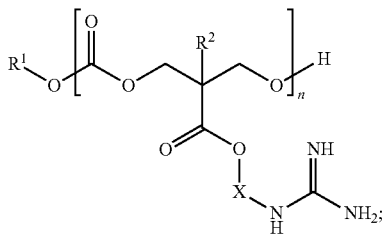

wherein "R¹" corresponds to a first functional group selected from the first group consisting of: a biotin group, a sugar group, a first alkyl group, and a first aryl group;
wherein "R²" corresponds to a second functional group selected from the second group consisting of a hydrogen, a second alkyl group, and a second aryl group;
wherein "X" corresponds to a spacer structure selected from the third group consisting of a third alkyl group and a third aryl group; and
wherein "n" corresponds to an integer greater than 1 and less than or equal to one thousand.

6. A method comprising:
enhancing an antimicrobial activity of an antirheumatic agent against Gram-negative bacteria by a combination therapy, wherein the combination therapy comprises the antirheumatic agent and a polycarbonate polymer functionalized with at least one guanidinium functional group, and wherein the antirheumatic agent comprises (2,3,4,6-Tetra-O-acetyl-1-thio-β-D-glucopyranosato-κS¹)(triethylphosphoranylidene)gold.

7. The method of claim 6, wherein the enhancing the antimicrobial activity of the antirheumatic agent comprises translocating the polycarbonate polymer across a cell membrane and interacting the polycarbonate polymer with a cytosolic member of a Gram-negative bacterium.

8. The method of claim 6, wherein the antimicrobial activity comprises increasing reactive oxygen species generation within the Gram-negative bacteria.

9. The method of claim 6, wherein the combination therapy mitigates an onset of resistance towards the antimicrobial activity by the Gram-negative bacteria.

10. The method of claim 6, wherein the polycarbonate polymer has a structure characterized by a chemical formula:

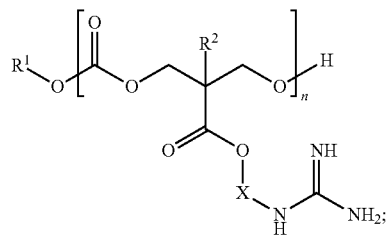

wherein "R¹" corresponds to a first functional group selected from the first group consisting of: a biotin group, a sugar group, a first alkyl group, and a first aryl group;
wherein "R²" corresponds to a second functional group selected from the second group consisting of a hydrogen, a second alkyl group, and a second aryl group;
wherein "X" corresponds to a spacer structure selected from the third group consisting of a third alkyl group and a third aryl group; and
wherein "n" corresponds to an integer greater than 1 and less than or equal to one thousand.

11. A method comprising:
treating a Gram-negative bacteria infection via a combination therapy that comprises a polycarbonate polymer functionalized with at least one guanidinium functional group and an antirheumatic agent comprising (2,3,4,6-Tetra-O-acetyl-1-thio-β-D-glucopyranosato-κS1)(triethylphosphoranylidene)gold, wherein the combination therapy reduces the Gram-negative bacteria infection.

12. The method of claim 11, further comprising:
translocating the polycarbonate polymer across a cell membrane of a bacterium of the Gram-negative bacteria infection; and
precipitating a cytosolic member of the bacterium via an interaction between the cytosolic member and the polycarbonate polymer.

13. The method of claim 12, further comprising:
increasing reactive oxygen species generation within bacterium of the Gram-negative bacteria infection as a result of the treating, resulting in cell apoptosis of the bacterium.

14. The method of claim 11, wherein the polycarbonate polymer has a structure characterized by a chemical formula:

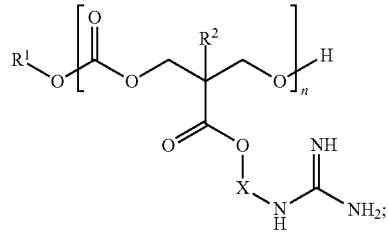

wherein "R¹" corresponds to a first functional group selected from the first group consisting of: a biotin group, a sugar group, a first alkyl group, and a first aryl group;
wherein "R²" corresponds to a second functional group selected from the second group consisting of a hydrogen, a second alkyl group, and a second aryl group;

wherein "X" corresponds to a spacer structure selected from the third group consisting of a third alkyl group and a third aryl group; and wherein "n" corresponds to an integer greater than land-less than or equal to one thousand.

15. The chemical composition of claim 1, wherein the antimicrobial activity comprises causing apoptosis of Gram-negative bacteria cells.

16. The method of claim 7, wherein the cytosolic member is selected from the group consisting of a protein, an enzyme, and a gene.

17. The method of claim 6, wherein the antimicrobial activity comprises causing apoptosis of Gram-negative bacteria cells.

18. The method of claim 12, wherein the cytosolic member is selected from the group consisting of a protein, an enzyme, and a gene.

19. The method of claim 11, wherein the combination therapy mitigates an onset of resistance towards antimicrobial activity of the combination therapy by Gram-negative bacterium of the Gram-negative bacteria infection.

20. The method of claim 19, wherein the antimicrobial activity comprises causing apoptosis of the Gram-negative bacterium.

* * * * *